US006682720B2

(12) United States Patent
Ryles et al.

(10) Patent No.: US 6,682,720 B2
(45) Date of Patent: *Jan. 27, 2004

(54) ZINC CITRATE BEADS IN ORAL COMPOSITIONS

(75) Inventors: Christine Watson Ryles, Milford, CT (US); David Robert Williams, Monroe, CT (US); Alexander George Ziemkiewicz, Shelton, CT (US); Jesus Antonio Urbaez, Waterbury, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/331,666

(22) Filed: Dec. 27, 2002

(65) Prior Publication Data

US 2003/0202945 A1 Oct. 30, 2003

Related U.S. Application Data

(63) Continuation-in-part of application No. 10/132,046, filed on Apr. 25, 2002.
(51) Int. Cl.$^7$ .................................................. A61K 7/16
(52) U.S. Cl. ........................ 424/49; 424/490; 424/641; 424/642; 424/643
(58) Field of Search ............................... 424/79–88, 490, 424/641, 642, 643

(56) References Cited

U.S. PATENT DOCUMENTS

| | | |
|---|---|---|
| 4,022,880 A | 5/1977 | Vinson et al. |
| 4,647,452 A | 3/1987 | Ritchey et al. |
| 4,749,575 A | 6/1988 | Rotman |
| 5,059,416 A | 10/1991 | Cherukuri et al. |
| 5,372,803 A | 12/1994 | Williams et al. |
| 5,824,292 A | 10/1998 | Carr et al. |
| 5,958,458 A | 9/1999 | Norling et al. |
| 6,156,120 A | 12/2000 | Heffels et al. |
| 6,284,283 B1 | 9/2001 | Costantino et al. |
| 6,316,029 B1 | 11/2001 | Jain et al. |
| 6,368,586 B1 | 4/2002 | Jacob et al. |
| 6,423,449 B1 | 7/2002 | Hong |

FOREIGN PATENT DOCUMENTS

EP  0 747 037  6/1995

*Primary Examiner*—Shep K. Rose
(74) *Attorney, Agent, or Firm*—Milton L. Honig

(57) ABSTRACT

An oral product, particularly for anti-tartar use, is provided which includes from about 0.001 to about 20% of beads which include a zinc salt, the zinc salt having an average particle size ranging from about 0.01 to about 5 mm, and a dental base.

10 Claims, No Drawings

ZINC CITRATE BEADS IN ORAL COMPOSITIONS

This is a continuation-in-part of Ser. No. 10/132,046 filed Apr. 25, 2002.

BACKGROUND OF THE INVENTION

1. Field of the Invention

The invention concerns anti-tartar dental compositions based on zinc citrate which have improved taste.

2. The Related Art

Tartar, known also as calculus, is a hard mineralized deposit which forms around teeth. This formation arises from deposition of crystals of calcium phosphate in the pellicle and the extracellular matrix of dental plaque. Various forms of calcium phosphate have been identified but the most difficult to remove and thermodynamically most stable form is called hydroxyapatite (HAP). Amorphous forms of calcium phosphate are believed to be the precursors of HAP. Regular brushing can usually remove the amorphous forms but is not fully effective to dislodge the final stable calculus form. Therefore it is desirable to prevent amorphous forms of calcium phosphate from transforming into HAP. The art has recognized that agents which interfere with the formation of HAP crystallization will be effective anti-tartar agents.

Zinc citrate has for many years been formulated into commercial dentifrices as an anti-tartar agent. Not only does it interfere with HAP crystallization, but it also has antibacterial activity. In the United Sates, zinc citrate has been formulated into toothpastes marketed under the Mentadent®, Close-Up® and Aim® brands sold by the Unilever operating companies. The technology is described in disclosures such as U.S. Pat. No. 4,022,880 (Vinson et al.), U.S. Pat. No. 4,647,452 (Ritchey et al.) and U.S. Pat. No. 5,372,803 (Williams et al.).

A major drawback of zinc citrate formulations is that the zinc ion imparts a relatively bitter taste. Smokers are particularly sensitive to the adverse taste.

Accordingly, it is an object of the present invention to provide an oral composition formulated with a zinc anti-tartar salt characterized by an improved taste.

These and other objects of the present invention will become more apparent in light of the detailed description and Examples which follow.

SUMMARY OF THE INVENTION

An oral product is provided comprising:
(i) from about 0.001% to about 20% of beads which include a zinc salt having an average particle size ranging from about 0.01 to about 5 mm; and
(ii) a dental base.

DETAILED DESCRIPTION OF THE INVENTION

Now it has been found that the bitter taste of zinc salts can be improved by incorporating the zinc salt in the form of relatively large active beads. On an equal zinc salt weight basis, the beads are at least as effective in anti-tartar activity as solubilized or dispersed non-complexed zinc salts of the known art.

Zinc salts usable for the present invention may include inorganic or organic counterions. Organic counterions include $C_2$–$C_{20}$ compounds, especially carboxylates. Preferred organic counterions include citrates, malates, malonates, maleates, adipates, succinates, acetates, propionates, lactates, tartrates, glycolates and combinations thereof. Most especially preferred is zinc citrate trihydrate.

Inorganic zinc salts are less preferred than the organic ones. These include counterions such as halides (e.g. chloride, bromide and iodide), sulfates, nitrates, phosphates and combinations thereof.

Amount of the beads may range from about 0.01 to about 20%, preferably from about 0.5 to about 10%, optimally from about 1 to about 5% by weight of the total oral product.

Optionally, a gum may be incorporated into the beads of the present invention. Illustrative gums are polysaccharides including sodium carboxymethyl cellulose (CMC), hydroxyethylcellulose, methylcellulose, ethylcellulose, hydroxypropyl cellulose, hydroxypropyl methylcellulose, gum tragacanth, gum arabic, gum karaya, pectin, carageenan, guar, xanthan gum, starch and combinations thereof. Most preferred are the cellulose type gums, especially sodium carboxymethyl cellulose (CMC). All molecular weight types of sodium CMC may be useful, although the medium viscosity grade such as the 9M grade is most suitable.

Beads of the present invention normally will contain essentially only zinc citrate. In a less preferred but useful embodiment, the beads may be formed by the complexion of the zinc salt with a gum in the presence of water to form gel particles. Relative weight ratios of the zinc salt to gum in this embodiment, may range from about 10,000:1 to about 10:1, preferably from about 1,000:1 to about 100:1 by weight.

In some embodiments of the present invention, water may be present within the beads. In those situations, the relative weight ratios of the zinc salt to water in the beads may range from about 50:1 to about 1:50, preferably from about 20:1 to about 1:1, optimally from about 10:1 to about 6:1 by weight.

Typically the amount of zinc salt in the beads is about 100%. However, in some embodiments the amount of zinc salt in the beads may range from about 15 to about 99%, sometimes from about 50 to about 95%, but optimally from about 90 to 100% by weight of the beads. When a gum is present, amounts of the gum within the bead may range from about 0.001 to about 2%, preferably from about 0.1 to about 1%, optimally from about 0.25 to about 0.5% by weight of the beads. The remainder of the bead composition generally is water present in amounts from about 1 to about 60%, preferably from about 2 to about 40%, optimally from about 5 to about 20% by weight of the beads.

Average particle size of the beads and also of the zinc salt may range from about 0.01 to about 5 mm, preferably from about 0.05 to about 3 mm, optimally from about 0.1 to about 2 mm. Bulk density of the beads may range from about 0.75 to about 0.95, preferably from 0.80 to 0.90, optimally from 0.81 to 0.84 gm/cc.

Beads according to the present invention are prepared prior to introduction into a dental base with other ingredients of the oral product. Zinc salt and any optional ingredients such as gum and water can be formed by mixing in a Hobart type blending apparatus.

In one embodiment, the beads are visually distinct in the dental base. This may be accomplished by the beads being opaque and the base being transparent. Alternatively, the beads may appear as clear bodies colored differently from a transparent or opaque base.

Besides the beads, the oral product will contain a dental base in an amount of about 80 to about 99% by weight.

Ingredients of the dental base may include humectants, thickeners, abrasives, anti-caries agents, surfactants, colorants, flavorants, opacifiers, water and a variety of special actives (e.g. desensitization agents such as potassium nitrate, peroxides and anti-bacterials such as triclosan).

Surfactants useful herein may be of the anionic, nonionic, cationic, zwitterionic or amphoteric type. Most preferred are sodium lauryl sulphate, sodium dodecylbenzene sulfonate and sodium lauryl sarcosinate. Amounts of the surfactant may range from about 0.5 to about 10%, preferably from about 1 to about 5% by weight of the dental base.

Humectants useful herein are usually polyols. Illustrative of this category are sorbitol, maltitol, mannitol, glycerin, propylene glycol, xylitol, hydrogenated corn syrup, polyethylene glycols and mixtures thereof. Amounts of the humectant may range from about 1 to about 60%, preferably from about 5 to about 50%, optimally from about 10 to about 40% by weight of the dental base.

Thickeners useful herein may be the same gums as utilized to complex with the zinc salts. However, these gums will be formulated into the dental base rather than into the pre-formed beads. Illustrative thickeners include sodium carboxymethyl cellulose, ethylcellulose, carageenan, xanthan gum, pectin, chemically modified starches and acrylates. The latter may be crosslinked polyacrylates such as Carbopol® 934. Inorganic thickeners are exemplified by silica aerogels and magnesium aluminum silicate, commercially available as Veegum®. Amounts of the thickener may range from about 0.01 to about 30%, preferably from about 0.1 to about 20%, optimally from about 0.5 to about 5% by weight of the dental base.

A fluoride anti-caries compound normally is usually present as part of the dental base. Illustrative of such fluoride compounds are sodium fluoride, potassium fluoride, calcium fluoride, stannous fluoride, stannous monofluorophosphate, sodium monofluorophosphate and copper fluoride. Most preferred is sodium fluoride. These sources should release anywhere from about 25 to about 5,000 ppm of fluoride ion. The anti-caries compound will normally be present in an amount from about 0.01 to about 5%, preferably from about 0.1 to about 2.5%, optimally from about 0.2 to about 1.5% by weight of the dental base.

Abrasives may also be present in the dental base. Illustrative materials include sodium metaphosphate, dicalcium phosphate, calcium pyrophosphate, silica, alumina, chalk, insoluble bicarbonate salts and mixtures thereof. Amounts of the abrasive may range from about 1 to about 80%, preferably from about 5 to about 50% by weight of the dental base.

When the oral compositions are gels, structurants may be necessary. Particularly useful as a structurant are potyoxyethylene-polyoxypropylene copolymers such as those sold under the trademark Pluronic®. These materials are also known as Potoxamers and employed in amounts from about 5 to about 30%, preferably from about 18 to about 25% by weight of the dental base.

Flavors may also be part of the dental base. These flavors may be based on oils of spearmint and peppermint. Examples of other flavoring materials include menthol, clove, wintergreen, eucalyptus and aniseed. Flavors may range in amount from about 0.1 to about 5% by weight of the dental base.

Sweetening agents may also be included in the dental base. Illustrative agents include saccharin, sodium cyclamate, aspartame, acesulfame, xylitol and combinations thereof at levels from about 0.1 to about 10% by weight of the dental base.

Other additives may also be incorporated into the dental base. These may be anti-tartar agents, colorants, preservatives, silicones, other synthetic or natural polymers such as Gantrez 597®, and mixtures thereof. Amounts of these other ingredients may range from about 0.01 to about 20% by weight of the dental base.

Water may be present in the dental base in amounts from about 1 to about 95%, preferably from about 10 to about 60%, optimally from about 20 to about 50% by weight of the dental base.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

The following examples will more fully illustrate the embodiments of this invention. All parts, percentages and proportions referred to herein and in the appended claims are by weight unless otherwise illustrated.

EXAMPLE 1

Zinc salt beads of the present invention were prepared in several different ways. One procedure utilized a Hobart bowl. Zinc citrate was added to the bowl and a 2% CMC solution was slowly added with mixing until the beads formed. They were then air dried and sieved. A second method for preparation was via a ribbon blender, again adding a 2% solution of CMC to the dry zinc citrate.

Fluidized bed technology can also be utilized for manufacture of the beads. By this procedure zinc citrate was suspended in the fluid bed reactor while a nozzle sprayed a 2% solution of CMC. The spray drier utilized for this purpose was a GPCG-5, ex Glatt Technologies with a Schlick 924 nozzle. This model was able to produce 5–7 kilogram batches. The 2% CMC solution was sprayed using a peristaltic pump along with pressurized air at the nozzle to atomize the spray. Achievement of optimum results required swift introduction of the CMC, use of cool air to fluidize, and maintenance of the product temperature during drying so that it stayed below 40° C. The relatively cool air prevented solids from sticking together before the beads were formed. During drying, the temperature quickly rose after water was removed. Care was taken not to over-dry which could lead to a frail bead. When the temperature reached 35° C., the batch was considered dried.

EXAMPLE 2

A typical get dentifrice composition incorporating the beads of this invention is described below.

TABLE I

| Component | Weight % |
| --- | --- |
| Sorbitol | 56.33 |
| Syloid 63X ® | 10.0 |
| Syloid 244 ® | 9.0 |
| Polyethylene glycol (1500 M.W.) | 5.00 |
| Ethyl alcohol | 2.1 |

TABLE I-continued

| Component | Weight % |
| --- | --- |
| Sodium lauryl sulfate | 1.6 |
| Menthol | 1.0 |
| Sodium monofluorophosphate | 0.8 |
| Cellulose gum | 0.4 |
| Sodium saccharin | 0.3 |
| Beads (Zinc Citrate/CMC in 200/1 ratio) | 0.5 |
| Water | Balance |

EXAMPLE 3

An opaque toothpaste with the beads of this invention has a formula as described below.

TABLE II

| Component | Weight % |
| --- | --- |
| Sorbitol | 15.0 |
| Glycerin | 3.0 |
| Calcium phosphate dihydrate, dibasic | 33.5 |
| Anhydrous calcium phosphate, dibasic | 5.0 |
| Titanium dioxide | 1.5 |
| Sodium lauryl phosphate | 1.5 |
| Carboxymethyl cellulose | 1.2 |
| Sodium monofluorophosphate | 0.8 |
| Peppermint oil | 0.6 |
| Sodium saccharin | 0.4 |
| Beads (Zinc Citrate/CMC in 300/1 ratio) | 1.0 |
| Water | Balance |

EXAMPLE 4

A comparative taste test is reported under this Example. Two formulas were evaluated. The first was according to Example 2 wherein zinc citrate was present in the form of complexed insoluble beads. A comparative experiment utilized the same formula as in Example 2 except that an equivalent amount of zinc citrate was solubilized within the formula rather than present as insoluble beads.

A flavor tasting panel was assembled consisting of thirteen persons. They rated the zinc citrate bead and the non-bead solubilized toothpaste after brushing, according to a series of organoleptic attributes. Ratings were on a scale of 1 to 5, where 1=poor and 5=excellent. After brushing with both products, the panelists chose their preference. Table III below lists results of the flavor test. Values provided in the second and third column are average ratings except for the "preference" entry where 9 people chose the bead product, 3 people chose the control (zinc citrate solubilized) and 1 person had no preference.

TABLE III

Flavor Test

| SENSORY PERCEPTION | ZINC CITRATE BEADS | ZINC CITRATE SOLUBILIZED |
| --- | --- | --- |
| Flavor | 4.00 | 3.31 |
| Strength | 3.92 | 3.77 |
| Foam | 3.38 | 3.54 |
| After Taste | 3.46 | 2.92 |
| Feel Clean | 4.00 | 3.69 |
| Impact | 3.92 | 3.38 |
| Overall Liking | 3.85 | 3.31 |
| Preference | 9.00 | 3.00 |

The tests indicate that the zinc citrate in bead form was favored in six of the seven taste categories. Only foam was found to be better in the comparative formula. The overall preference, by a wide margin, was for zinc citrate in the bead form rather than solubilized.

EXAMPLE 5

Zinc citrate beads were prepared in a Chilsonator®. This equipment compacts the zinc citrate powder by forcing the powder between two counter rotating rolls. As the volume decreases through a region of maximum pressure, the material is formed into a solid compact or sheet. As the rolls turn toward each other, the material in a slip region moves downward at a rate less than the surface speed of the rolls. In a nip region, the materials are caught or trapped by the rolls and move at a same speed as the roll surface, this forces the material through the region of maximum pressure, which is on a line between the centers of the two rolls.

After compaction, the resultant material is fed into a FitzMill® granulator to gently cut the compacted material into beads which are separated by screens into appropriate sizes.

For the present Example, the Chilsonator® was operated at a roll speed of 5.0 rpm, a Vertical Screw Feed of 80 rpm, a Horizontal Screw Feed of 15 rpm, and a pressure of 700 psi. The angle of repose of zinc citrate was 45°. The loose density of the zinc citrate bead was 0.61 g/cc. The compact thickness of the resultant ribbon from the Chilsonator® before milling was 0.15 inches. After granulation, the resultant particles were sieved to obtain samples of different average particle size. These sizes were evaluated in a dental base outlined under Table I above.

Twelve people participated in a bead evaluation panel. All brushed their teeth with four products containing different particle size beads, all of which dentifrices were fielded blind. The study was cross-over in nature, the products being randomized and panelists brushing with two products during the course of one day and then two more products the following day. After each brushing, a brief questionnaire was filled out. The tables below display the results. The term "sensory" refers to a combination score of flavor while brushing, aftertaste and mouthfeel while brushing.

TABLE IV

Particle Size of Zinc Citrate Beads vs. Sensory

| Average Particle (mm) | Sensory Score |
| --- | --- |
| 1.35 | 17 |
| 0.65 | 66 |
| 0.225 | 58 |
| <0.15 | 25 |

TABLE V

Panelist Rating of Excellent For Overall Liking

| Average Particle Size (mm) | % Rates Excellent |
| --- | --- |
| 1.35 | 0 |
| 0.65 | 25 |
| 0.225 | 25 |
| <0.15 | 7 |

TABLE VI

| Panelists Rating For Texture | |
|---|---|
| Average Particle Size (mm) | % Texture Rating |
| 1.35 | 32 |
| 0.65 | 91 |
| 0.225 | 91 |
| <0.15 | 83 |

Overall sensory properties peaked in the average particle size area between 0.65 and 0.225 mm. This was also the area within which maximum ratings for overall liking and texture were given.

The foregoing description and examples illustrate selected embodiments of the present invention. In tight thereof variations and modifications will be suggested to one skilled in the art, all of which are within the spirit and purview of this invention.

What is claimed is:

1. An oral product comprising:
   (i) from about 0.001% to about 20% of beads which comprise a zinc salt that has an average particle size ranging from about 0.01 to about 5 mm; and
   (ii) a dental base.

2. The composition according to claim 1 wherein the zinc salt is zinc citrate trihydrate.

3. The composition according to claim 1 wherein the zinc salt has an average particle size ranging from about 0.1 to about 2 mm.

4. The composition according to claim 1 wherein the beads further comprise a gum.

5. The composition according to claim 4 wherein the gum is a cellulose.

6. The composition according to claim 5 wherein the gum is sodium carboxymethyl cellulose.

7. The composition according to claim 4 wherein the ratio of zinc salt to gum ranges from about 1,000:1 to about 100:1.

8. The composition according to claim 1 wherein the dental base comprises a material selected from the group consisting of humectants, thickeners, surfactants, colorants, flavorants, anti-caries agent, abrasives, opacifiers, water and combinations thereof.

9. The composition according to claim 1 wherein the beads are pre-formed and then combined into the dental base.

10. The composition according to claim 1 wherein the beads are opaque and the dental base is transparent.

* * * * *